United States Patent
Wu

(10) Patent No.: US 9,782,241 B2
(45) Date of Patent: Oct. 10, 2017

(54) ORTHODONTIC STRUCTURE CAPABLE OF IMPLANTING IMPLANTS AND STRAIGHTENING TEETH

(71) Applicants: CHIEN-TE, Taipei (TW); BIOMATE MEDICAL DEVICES TECHNOLOGY CO., LTD., Kaohsiung (TW)

(72) Inventor: Chien-Te Wu, Taipei (TW)

(73) Assignees: Chien-Te Wu, Kaohsiung (TW); Biomate Medical Devices Technology Co., Ltd., Kaohsiung (TW)

(*) Notice: Subject to any disclaimer, the term of this patent is extended or adjusted under 35 U.S.C. 154(b) by 0 days.

(21) Appl. No.: 14/995,342

(22) Filed: Jan. 14, 2016

(65) Prior Publication Data
US 2017/0202647 A1    Jul. 20, 2017

(51) Int. Cl.
*A61C 7/14*    (2006.01)
*A61C 7/22*    (2006.01)
*A61C 8/00*    (2006.01)

(52) U.S. Cl.
CPC .............. *A61C 8/0096* (2013.01); *A61C 7/14* (2013.01); *A61C 7/22* (2013.01)

(58) Field of Classification Search
CPC .. A61C 7/143; A61C 7/14; A61C 7/22; A61C 8/0096
USPC ........................... 433/8–24, 172–176
See application file for complete search history.

(56) References Cited

U.S. PATENT DOCUMENTS

| | | | | |
|---|---|---|---|---|
| 4,669,980 A * | 6/1987 | Degnan | ..................... | A61C 7/14 433/16 |
| 4,988,292 A * | 1/1991 | Rosen | ...................... | A61C 7/00 433/10 |
| 5,836,768 A * | 11/1998 | Huskens | ................... | A61C 7/00 433/172 |
| 6,312,259 B1 * | 11/2001 | Kvarnstrom | ......... | A61C 8/0075 433/173 |
| 2004/0265768 A1 * | 12/2004 | Tuneberg | ............... | A61C 7/282 433/17 |
| 2006/0257811 A1 * | 11/2006 | Ohki | ........................ | A61C 7/10 433/18 |
| 2011/0165532 A1 * | 7/2011 | Benvegnu' | ............... | A61C 7/00 433/18 |
| 2011/0300503 A1 * | 12/2011 | Benvegnu | ................ | A61C 7/00 433/22 |

(Continued)

*Primary Examiner* — Nicholas Lucchesi
*Assistant Examiner* — Drew Folgmann
(74) *Attorney, Agent, or Firm* — Rosenberg, Klein & Lee

(57) ABSTRACT

An orthodontic structure includes a body where at least one connecting hole is formed, a fastening part disposed on the body and fastened to an implant, and at least one traction assembly connected to the body. The traction assembly includes an orthodontic table and an adjustment part extending outwards from the orthodontic table to engage the connecting hole. The orthodontic table has at least one locking recess capable of holding a metal wire in place. The orthodontic structure is connected to the implant which is embedded in an alveolar bone in advance to provide a requisite anchorage effect required by orthodontics. Thus, the implant treatment and the orthodontic treatment can be concurrently executed to shorten the treatment time for straightening teeth and attain good implanting and straightening effects.

7 Claims, 6 Drawing Sheets

(56) References Cited

U.S. PATENT DOCUMENTS

2015/0099242 A1* 4/2015 Cho ................... A61C 8/0048
433/201.1

* cited by examiner

ORTHODONTIC STRUCTURE CAPABLE OF IMPLANTING IMPLANTS AND STRAIGHTENING TEETH

BACKGROUND OF THIS INVENTION

1. Field of this Invention

This invention relates to an orthodontic design fixed on an implant and relates particularly to an orthodontic structure capable of implementing the implant treatment and the orthodontic treatment.

2. Description of the Related Art

The purpose of orthodontic treatment is to correct or straighten the misalignment of teeth, so-called "abnormal bites", and help people retrieve the normal occlusion. Generally, most patients who need the orthodontic treatment are children or teenagers. If the treatment can be made at an early stage, the possibility of malocclusion can be reduced. Nowadays, more and more adults accept the orthodontic treatment for having a good facial appearance. However, if the patient has missing and irregular teeth and needs concurrent remedies, the dentist needs to set up different processes for straightening and correcting according to the state of the oral cavity. For example, if the irregular teeth is slight, the orthodontic treatment specialized in straightening teeth can come before the implant treatment specialized in the missing teeth. If the patient has serious irregular and missing teeth, the orthodontic treatment should come after the implant treatment. In general, there is a waiting period for the healing of the implant treatment or for straightening teeth, no matter which treatment comes first. The latter treatment cannot proceed unless the former treatment completes. It is noted that the duration of either treatment, including the waiting period, may need at least three to six months, one year or even years. In other words, it usually needs more than two years to complete the entire processes for treatment. This situation prolongs the entire treatment time. Furthermore, there must be additional anchorage surgery in the treatment process, so the treatment time cannot be shortened. The prolongation of the period easily makes the daily life of the patient inconvenient and wastes time.

SUMMARY OF THIS INVENTION

An object of this invention is to provide an orthodontic structure which reduces the time of making any extra anchorage and omits extra surgery to shorten the treatment period of straightening or correcting teeth, thereby carrying out the implant treatment and the orthodontic treatment at the same time and increasing the effect of straightening teeth.

An orthodontic structure of this invention includes a body, a fastening part disposed on the body and fastened to an implant of an artificial root, and at least one traction assembly connected to the body. At least one connecting hole is formed on the body. The traction assembly includes an orthodontic table where at least one locking recess is formed for holding a metal wire in place and an adjustment part extending outwards from the orthodontic table. The adjustment part engages the connecting hole. Accordingly, when the fastening part is positioned on the implant embedded into the alveolar bone to cause a combination between the orthodontic structure and the implant, the positioning state of the orthodontic structure conduces to a reduction in the time of implementing any extra anchorage process. The metal wire is held by the orthodontic table of the traction assembly so that the orthodontic table and peripheral orthodontic braces by which the metal wire is held can be in mutual traction and help each other. Thus, when the implant treatment is executed, the orthodontic treatment can also be carried into execution. Thus, the needed treatment time for implant and orthodontic treatment can be largely reduced, and good implanting and straightening effects can be attained.

Preferably, the body has at least one binding recess formed thereon, preferably located between a top face of the body and the connecting hole.

Preferably, the body has at least one engaging hole, which may be formed apart from the connecting hole, so that an engagement unit can engage the engaging hole.

Preferably, the orthodontic table has peripheral faces, and more than one locking recess can be formed on any, some or all of the peripheral faces. Thus, the metal wire can be held by any of the locking recesses.

Preferably, the orthodontic table has at least one fixing hole formed thereon, preferably going through the peripheral faces of the orthodontic table.

The advantages of this invention are more apparent upon reading the following descriptions in conjunction with the drawings.

DETAILED DESCRIPTION OF THE PREFERRED EMBODIMENTS

Figure 1:
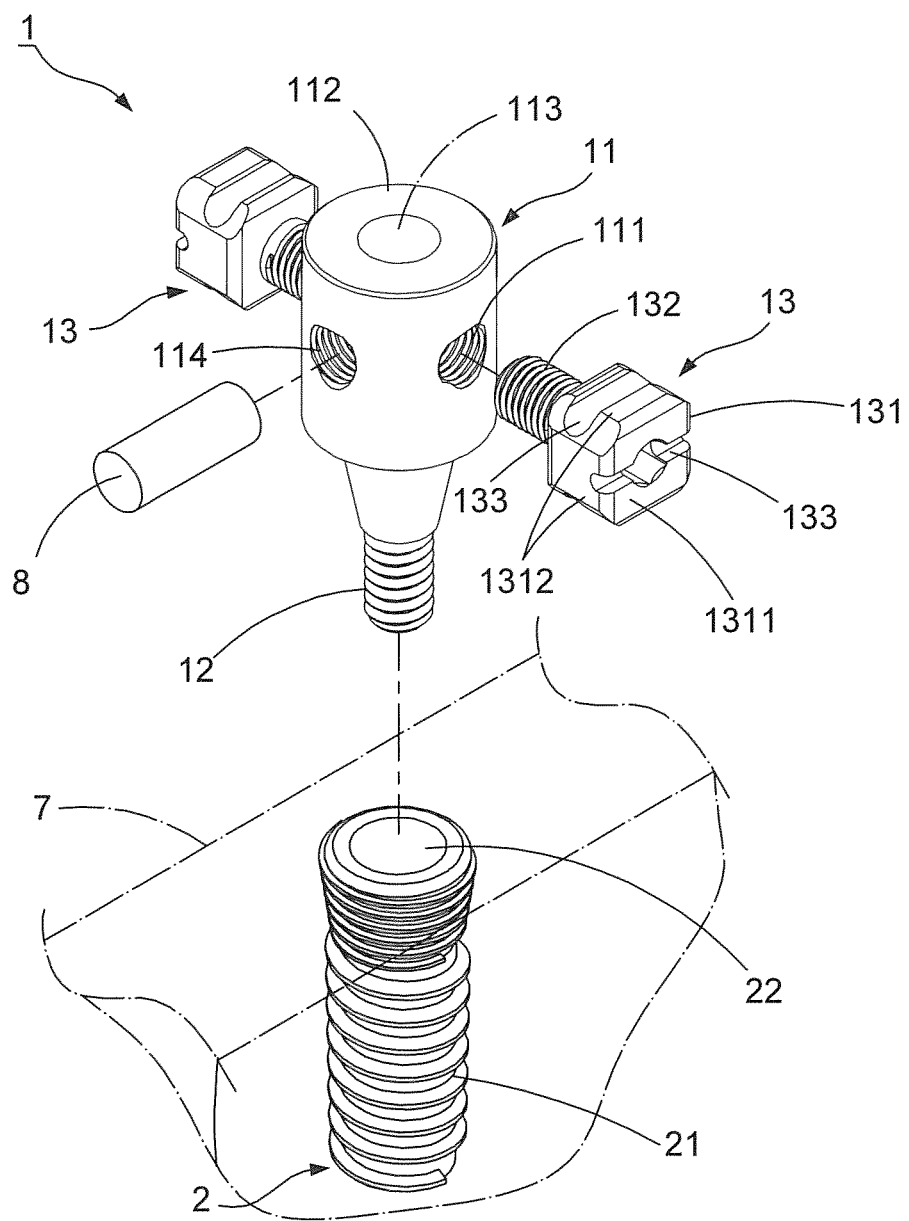
FIG. 1 is an exploded view showing a first preferred embodiment of this invention.
Figure 2:
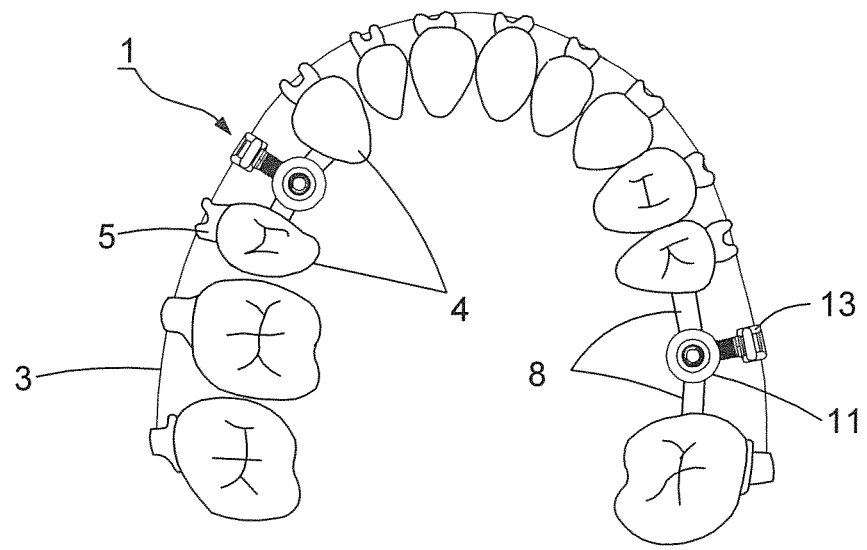
FIG. 2 is a schematic view showing the first preferred embodiment in use.

Referring to FIG. 1, an orthodontic structure 1 of a first preferred embodiment of this invention is fastened to an implant 2 of an artificial root and is used to catch a metal wire 3, shown in FIG. 2, for straightening or correcting teeth 4. The implant 2 has a positioning part 21 embedded into an alveolar bone 7 (as sketchily shown) and a screwing hole 22 defined through a top face of the implant 2. Further, the orthodontic structure 1 includes a body 11, a fastening part 12 disposed on one side of the body 11, and at least one traction assembly 13 connected to another side of the body 11. The fastening part 12 is screwed into the screwing hole 22 of the implant 2 for positioning.

The body 11, preferably a cylinder, has at least one connecting hole 111 formed thereon, a driving socket 113 formed through a top face 112 of the body 11 for allowing an entry of a drive tool (not shown), and at least one engaging hole 114 formed thereon and spaced apart from the connecting hole 111. There can be multiple connecting holes 111. In this and following preferred embodiments, two connecting holes 111 are taken as an example, and the connecting holes 111, as shown in FIG. 1, are restively formed on opposite sides of a periphery of the body 11. Each of the connecting holes 111 provides an engagement with the traction assembly 13. Further, the engaging hole 114 is also formed on the periphery of the body 11 between the connecting holes 111. There can also be multiple engaging holes 114. Herein, it is adopted that there are two engaging holes 114, each of which allows an insertion of an engagement unit 8. The engagement unit 8 can be an elastic spring (as schematically shown in FIG. 1) or other suitable designs.

Still referring to FIG. 1, the traction assembly 13 has an orthodontic table 131 and an adjustment part 132 extending outwards from the orthodontic table 131 to provide an engagement with the connecting hole 111. The orthodontic table 131 further has at least one locking recess 133 formed thereon. Preferably, there can be multiple locking recesses 133 formed on different peripheral faces of the orthodontic table 131. For example, FIG. 1 shows that one locking recess 133 is recessed into a side peripheral face 1311 of the orthodontic table 131, and another locking recess 133 is recessed into another peripheral face 1312 which may be vertical to the side peripheral face 1311. Thus, the metal wire 3 can be gripped by any of the locking recesses 133 and becomes positioned.

In use, the operation of this invention can start with implant surgery or treatment. Referring to FIG. 1 and FIG. 2, the implant treatment is executed by embedding the positioning part 21 of the implant 2 into a predrilled bore on the alveolar bone 7. When the implant 2 is integrated into the alveolar bone 7 for osseointegration, the dentist can choose a better way to use the orthodontic structure 1 according to teeth of a patient. For example, if the oral cavity of patient has a serious problem and needs to be well straightened, two traction assemblies 13 can be connected to the body 11, as shown in FIG. 1, to concurrently correct the teeth at an internal side and an external side of the teeth 4. If the dentist considers that the problem is slight, only one traction assembly 13 can be connected to the body 11, as shown in FIG. 2.

After deciding the installation of the traction assembly 13, a drive tool (not shown) is put into the driving socket 113 to threadedly fasten the fastening part 12 to the screwing hole 22 of the implant 2. Thus, the orthodontic structure 1 is firmly fixed to the implant 2. Then, the entry distance of the adjustment part 132 into the connecting hole 111 can be properly adjusted according to the distance between peripheral teeth 4 beside the orthodontic structure 1, thereby allowing the side peripheral face 1311 of the orthodontic table 131 and orthodontic braces 5 which are attached to the peripheral teeth 4 to be set on a same horizontal line, as shown in FIG. 2 where The orthodontic table 131 and the orthodontic braces 5 can be in juxtaposition. Thus, the problem that the orthodontic process does not go smoothly can be solved. Concurrently, to confirm that the artificial tooth or teeth (not shown) can be well placed into a space formed by the aforementioned implant process, one end of the engagement unit 8 is inserted into the engaging hole 114, and the other end thereof props against the side of the peripheral teeth 4. Finally, the metal wire 3 is attached to the orthodontic braces 5 of the teeth 4 and is held by the locking recess 133 of each orthodontic table 131. It is noted that the dentist can decide which locking recess 133 is suitable to position the metal wire 3 according to the state of the teeth and the plan for orthodontics. The metal wire 3 can be held by the locking recess 133 formed on the side peripheral face 1311 or by any of the locking recesses 133 formed on another peripheral faces 1312.

From above, when the orthodontic structure 1 is positioned, a requisite anchorage effect for orthodontics is obtained which allows an adjustment in different processes of the orthodontic treatment. Thus, an initial preparation for the orthodontic treatment is done.

During a waiting period for the implant treatment, the orthodontic structure 1 and the orthodontic braces 5 can be used to start the orthodontic treatment directly, thereby reducing the time of having an extra anchorage action and prevent the occurrence of having extra surgery. Every time the metal wire 3 is adjusted in every different stage, the teeth 4 attached to the orthodontic braces 5 and the orthodontic structure 1 which are subject to the adjustment of the metal wire 3 allow the teeth 4 which need to be straightened to move slightly and slowly on the alveolar bone 7, and the orthodontic table 131 and peripheral orthodontic braces 5 by which the metal wire 3 is held are also in mutual traction and support each other. Concurrently, when the orthodontic process proceeds in order to move the teeth 4 to their desirable positions, the engagement units 8 connected to two sides of the body 11 subject the side of the peripheral teeth 4 to an adjustment to prevent the peripheral teeth 4 from getting too close to each other. After the orthodontic process is completed, the artificial tooth can be smoothly put on the space where the implant is initially located. Thus, the implant treatment and the orthodontic treatment can be executed concurrently to shorten and save the treatment time for implantation and orthodontics, prevent a daily inconvenience caused by a long treatment period and obtain good implanting and straightening effects.

Figure 3:
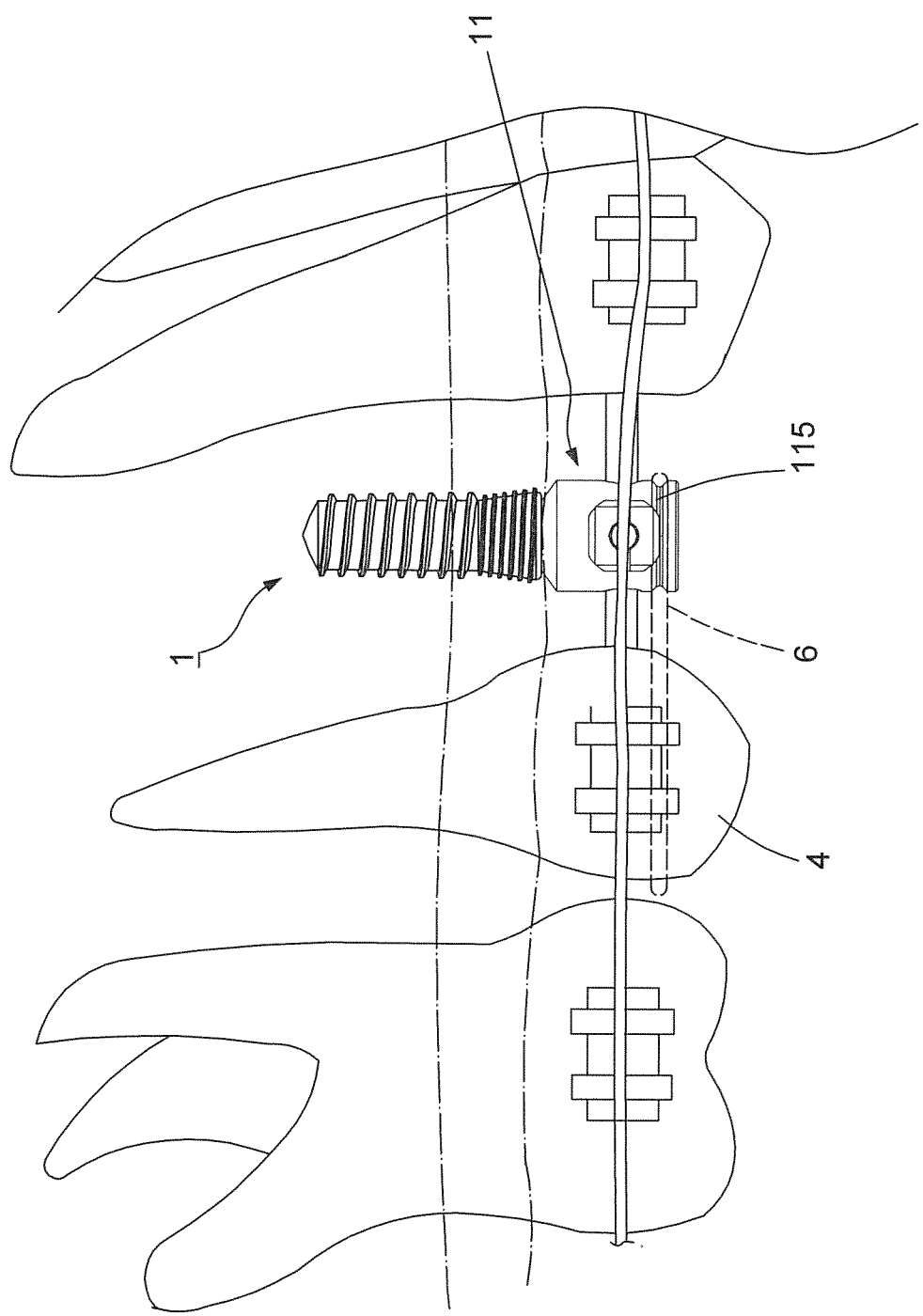
FIG. 3 is a schematic view showing a second preferred embodiment of this invention.

Referring to FIG. 3, an orthodontic structure 1 of a second preferred embodiment has the same elements as the first preferred embodiment. The concatenation of correlated elements is still the same as the first preferred embodiment. This preferred embodiment is characterized in that at least one binding recess 115 is formed on the body 11 and located between the top face 112 and the connecting hole 111 which is invisible in this figure. The body 11 can also have multiple binding recesses 115 formed thereon to adapt to different remedies for straightening teeth 4. One end of an orthodontic rubber band 6 is inserted in the binding recess 115, and the other end thereof is positioned on the tooth 4 beside the orthodontic structure 1, as schematically shown.

When the implant treatment and the orthodontic treatment concur, the binding recess 115 helps correct the canting tooth or teeth 4 beside the orthodontic structure 1. Specifically, two ends of the orthodontic rubber band 6 are held between the binding recess 115 and the canting tooth 4 to gradually straighten the tooth 4 under a tension force of the orthodontic rubber band 6. The orthodontic rubber band 6 also adjusts the requisite tension as required by the orthodontics. Accordingly, every time the straightened tooth 4 is adjusted by the tension force, the problem that the tooth 4 cants or deviates during the orthodontic treatment can be solved, and the straightened tooth 4 can gradually move to a desirable place and become positioned. Thus, the treatment period for implanting and straightening can be shortened, and the implant treatment and the orthodontic treatment can work concurrently.

Figure 4:
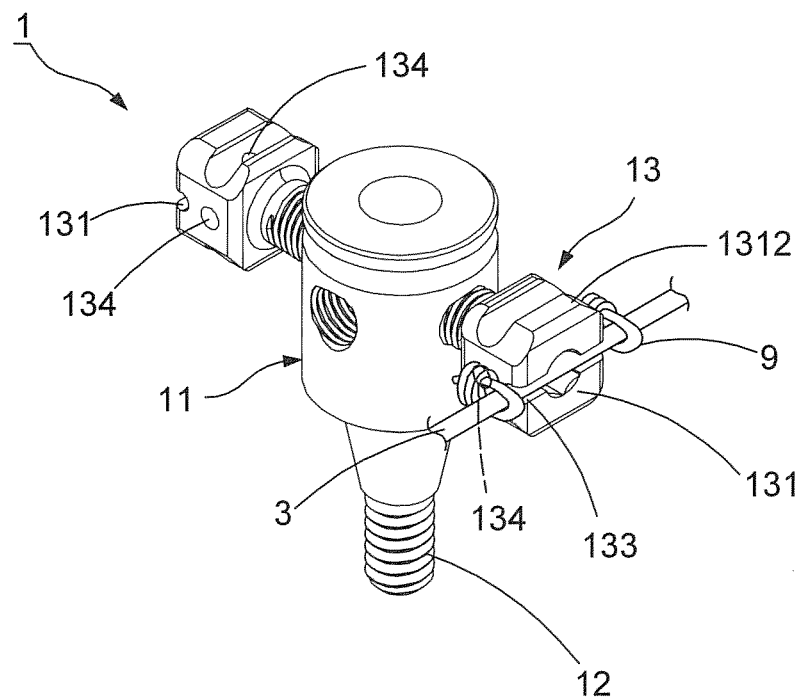
FIG. 4 is a perspective view showing a third preferred embodiment of this invention.
Figure 5:
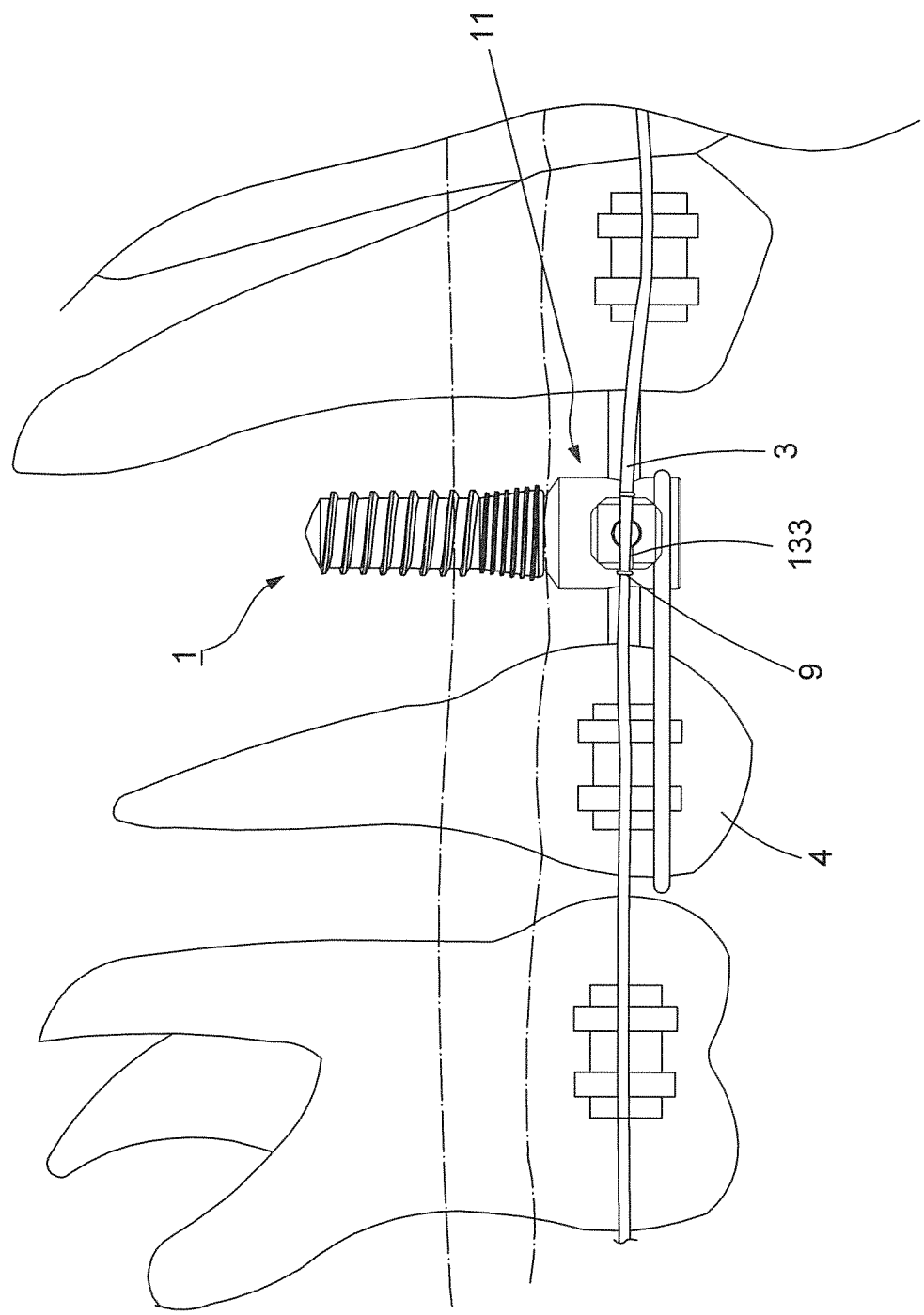
FIG. 5 is a schematic view showing the third preferred embodiment in use.
Figure 6:
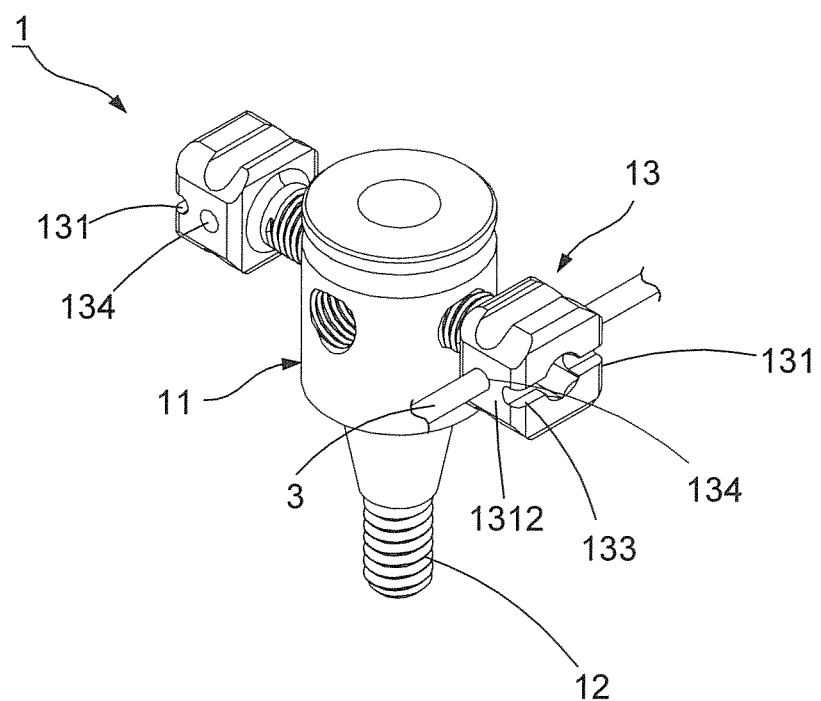
FIG. 6 is a perspective view showing a variation of the third preferred embodiment.

Referring to FIG. 4, an orthodontic structure 1 of a third preferred embodiment has a body 11, a fastening part 12 and at least one traction assembly 13. The concatenation of correlated elements is still the same as the previous preferred embodiment. This preferred embodiment is characterized in that at least one fixing hole 134 is formed on the orthodontic table 131. The fixing hole 134 goes through the peripheral faces 1312 of the orthodontic table 131. A support unit 9, as shown in FIGS. 4 and 5, can extend through the fixing hole 134 for positioning. Alternatively, the metal wire 3, as shown in FIG. 6, can extend through the fixing hole 134 directly for positioning. If the metal wire 3 is to be held by the locking recess 133, two ends of the support unit 9 which project outwards from the fixing hole 134 as shown in FIGS. 4 and 5 catches and limits the metal wire 3 and makes sure that the metal wire 3 is put in the locking recess 133. Thus, the escape of the metal wire 3 from the orthodontic structure 1 caused by neglectfulness of the patient during the orthodontic period can be prevented, and the full orthodontic course can go smoothly and stably in order to execute the implant treatment and the orthodontic treatment concurrently and conduce to good implanting and straightening effects.

To sum up, this invention takes advantage of the orthodontic structure which is fixed on the implant embedded into the alveolar bone in advance to reduce the time of having any extra anchorage additionally and omit additional surgery. Thus, the treatment period of the orthodontics can be shortened. The traction assembly can be used to hold the metal wire in place, so the implant treatment and the orthodontic treatment can be executed concurrently. Thus, a good implant treatment and a good effect of straightening teeth can be obtained.

While the embodiments of this invention are shown and described, it is understood that further variations and modifications may be made without departing from the scope of this invention.

What is claimed is:

1. An orthodontic system for holding a metal wire in a fixed position for straightening teeth of a patient, said orthodontic system comprising:
    an implant adapted for releasable engagement within an alveolar bone of said patient;
    a body having a fastening part disposed thereon releasably fastened to said implant, said body extending in a first direction; and
    at least one traction assembly connected to extend from said body, wherein said body has at least one threaded connecting hole formed therein, said traction assembly engaging the connecting hole to be adjustably extendable in a direction substantially perpendicular to said first direction and fixed in position relative to said body;
    said at least one traction assembly including an orthodontic table and an adjustment part extending outwards from said orthodontic table, said adjustment part threadedly engageable with said threaded connecting hole, said orthodontic table having at least one locking recess formed within at least one surface of said orthodontic table configured for holding said metal wire in place for straightening teeth.

2. The orthodontic system according to claim 1, wherein said body has at least one binding recess formed therein.

3. The orthodontic system according to claim 1, wherein said body has at least one engaging hole for allowing an engagement unit to engage therewith.

4. The orthodontic system according to claim 2, wherein said body has at least one engaging hole for allowing an engagement unit to engage therewith.

5. The orthodontic system according to claim 1, wherein said orthodontic table defines a plurality of peripheral faces having a plurality of locking recesses formed therein, said metal wire being held by a selected one of said locking recesses.

6. The orthodontic system according to claim 1, wherein said orthodontic table has at least one fixing hole formed therein.

7. The orthodontic system according to claim 5, wherein said orthodontic table has at least one fixing hole formed therein.

* * * * *